US009848928B2

(12) United States Patent
Foley et al.

(10) Patent No.: US 9,848,928 B2
(45) Date of Patent: Dec. 26, 2017

(54) SPINAL IMPLANT SYSTEM AND METHODS OF USE (71) Applicant: Warsaw Orthopedic, Inc., Warsaw, IN (US)

(72) Inventors: Kevin Foley, Germantown, TN (US); Gregory C. Marik, Collierville, TN (US); Newton Metcalf, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/627,202

(22) Filed: Feb. 20, 2015

(65) Prior Publication Data

US 2016/0242826 A1 Aug. 25, 2016

(51) Int. Cl.
*A61B 17/70* (2006.01)
*A61B 17/86* (2006.01)
*A61B 90/00* (2016.01)

(52) U.S. Cl.
CPC ...... *A61B 17/8635* (2013.01); *A61B 17/7032* (2013.01); *A61B 2090/031* (2016.02); *A61B 2090/037* (2016.02)

(58) Field of Classification Search
USPC ........................................................ 606/266
See application file for complete search history.

(56) References Cited

U.S. PATENT DOCUMENTS

| 5,466,237 | A  | * | 11/1995 | Byrd, III    | A61B 17/7037 606/272 |
| 5,743,914 | A  | * | 4/1998  | Skiba        | A61B 17/8625 411/412 |
| 8,579,948 | B2 | * | 11/2013 | Biedermann   | A61B 17/7098 606/301 |
| 2001/0021852 | A1 | * | 9/2001 | Chappius     | A61B 17/3472 600/300 |
| 2006/0116677 | A1 | * | 6/2006 | Burd         | A61B 17/7032 74/1 R |
| 2006/0253120 | A1 | * | 11/2006 | Anderson    | A61B 17/808 606/86 R |
| 2007/0106123 | A1 | * | 5/2007 | Gorek       | A61B 1/32 600/210 |
| 2009/0222044 | A1 | * | 9/2009 | Gorek       | A61B 17/0218 606/279 |
| 2010/0249856 | A1 | * | 9/2010 | Iott         | A61B 17/7085 606/86 A |
| 2012/0316605 | A1 | * | 12/2012 | Palagi      | A61B 17/7037 606/305 |
| 2013/0012954 | A1 | * | 1/2013 | Paroth       | A61B 17/7037 606/104 |

(Continued)

Primary Examiner — Jan Christopher Merene (57) ABSTRACT

A method comprising the steps of: providing an implant support including a first portion frangibly connected to a second portion that defines an implant cavity and supports a bone fastener; connecting a surgical introducer instrument with the implant support and engaging the surgical introducer instrument with the bone fastener; percutaneously introducing the surgical introducer instrument, implant support and bone fastener assembly to a surgical site including tissue; attaching the second portion with the bone fastener to the tissue; and removing the first portion from the second portion. Systems, fasteners and instruments are disclosed.

16 Claims, 4 Drawing Sheets

(56) References Cited

U.S. PATENT DOCUMENTS

2013/0150864 A1\* 6/2013 Marik ................ A61B 17/8888
 606/104
2016/0008034 A1\* 1/2016 Stokes ............... A61B 17/7085
 606/278

\* cited by examiner

SPINAL IMPLANT SYSTEM AND METHODS OF USE

TECHNICAL FIELD

The present disclosure generally relates to medical devices for the treatment of spinal disorders, and more particularly to a surgical implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In some embodiments, a method of treating a spine is provided. The method comprising the steps of: providing an implant support including a first portion frangibly connected to a second portion that defines an implant cavity and supports a bone fastener; connecting a surgical introducer instrument with the implant support and engaging the surgical introducer instrument with the bone fastener; percutaneously introducing the surgical introducer instrument, implant support and bone fastener assembly to a surgical site including tissue; attaching the second portion with the bone fastener to the tissue; and removing the first portion from the second portion. In some embodiments, fasteners and instruments are disclosed.

In some embodiments, a spinal implant system is provided. The spinal implant system comprises a percutaneous implant support extending between a first end and a second end. The implant support includes a first portion frangibly connected to a second portion that defines an implant cavity. The second end includes a member that is flexible relative to the second end and configured to support a bone fastener.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a spinal implant system including one or more surgical instruments and implants. In some embodiments, the systems and methods of the present disclosure are employed with a spinal joint fixation, for example, with a cervical, thoracic, lumbar and/or sacral region of a spine. In one embodiment, the spinal implant system includes an implant comprising a bone fastener, such as, for example, a pedicle bone screw.

In some embodiments, the spinal implant system includes a pedicle access needle/pedicle screw combination. In some embodiments, the spinal implant system is employed with a method of minimally invasive pedicle screw fixation. In some embodiments, the pedicle access needle/pedicle screw combination reduces surgical steps, the number of instruments and implant inventory in minimally invasive pedicle screw fixation procedures.

In some embodiments, the spinal implant system includes an in-situ pedicle access needle/multi-axial screw (MAS) assembly delivery system. In some embodiments, the spinal implant system includes pedicle access needle and screw components. In some embodiments, the spinal implant system includes a surgical instrument, such as, for example, a pedicle access tube having a MAS saddle and breakoff extender tabs. In some embodiments, the MAS saddle includes a gasket and/or a sleeve. In some embodiments, the MAS saddle includes a silicon/polymer gasket and/or sleeve. In some embodiments, the gasket and/or sleeve allows the pedicle access tube to advance through tissue in an introduction position. In some embodiments, the gasket and/or sleeve resists and/or prevents tissue from moving into a distal opening of the pedicle access tube. In some embodiments, the spinal implant system includes a pedicle screw having a pedicle access stylet tip. In some embodiments, the spinal implant system includes a pedicle screw having bone screw threads and a trocar type stylet tip. In some embodiments, the spinal implant system includes a surgical instrument, such as, for example, a pedicle access introducer/screw driver.

In some embodiments, the present spinal implant system is employed with a method of assembly that includes the steps of selecting a universal saddle/pedicle access tube for a selected surgical procedure. In some embodiments, the method of assembly includes the step of selecting an appropriate screw size, which may be selected from one or a plurality of alternately sized and configured screws, for example, having multiple diameters and/or lengths available. In some embodiments, the method of assembly includes the step of introducing a bone screw to a pedicle access tube such that a pedicle access tip of the bone screw is exposed and/or selectively positioned. In some embodiments, the method of assembly includes the step of attaching a surgical instrument, such as, for example, an introducer/driver to the pedicle access assembly.

In some embodiments, the present spinal implant system is employed with a method of treating a spine with a pedicle access assembly that comprises the step of percutaneously introducing the pedicle access assembly to a pedicle. In some embodiments, the method of treating a spine includes the step of driving the pedicle screw into the pedicle. In some embodiments, the method of treating a spine includes the step of providing a pedicle access tube that includes one or more graft delivery windows to minimally invasively deliver graft material to an anatomic location. In some embodiments, the method of treating a spine includes the step of removing a driver and introducing a connective element, such as, for example, a spinal rod. In some embodiments, the method of treating a spine includes the step of introducing a set screw and breaking off the extender tabs.

In some embodiments, the present spinal implant system comprises surgical instruments that include image guided technologies, such as, for example, surgical navigation components employing emitters and sensors, which may be employed to track introduction and/or delivery of the components of the surgical system including the surgical instruments to a surgical site.

In some embodiments, the present spinal implant system comprises an implant support configured to separate, for example, by mechanical failure at a predetermined force. In some embodiments, the implant support includes a break away portion that fractures at a predetermined torque.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
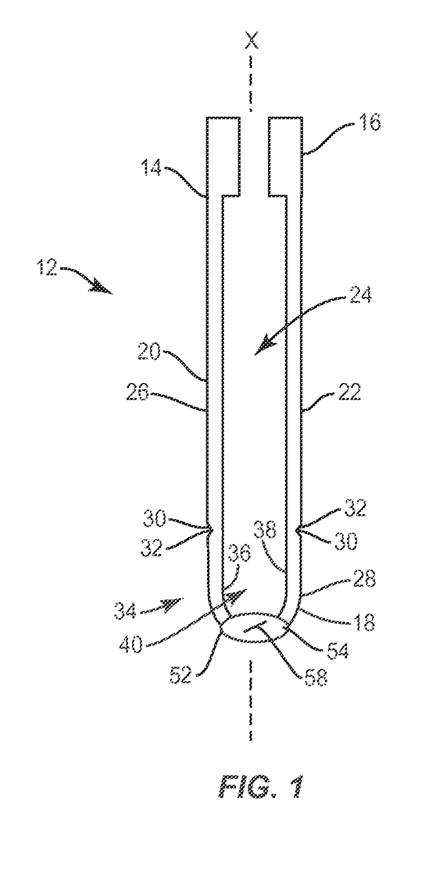
FIG. 1 is a side view of components of one embodiment of a spinal implant system in accordance with the principles of the present disclosure.
Figure 2:
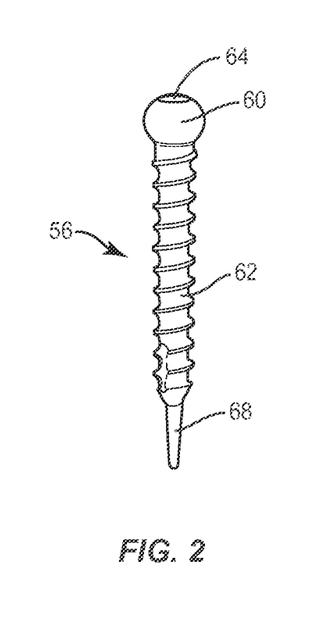
FIG. 2 is a side view of components of one embodiment of a spinal implant system in accordance with the principles of the present disclosure.
Figure 3:
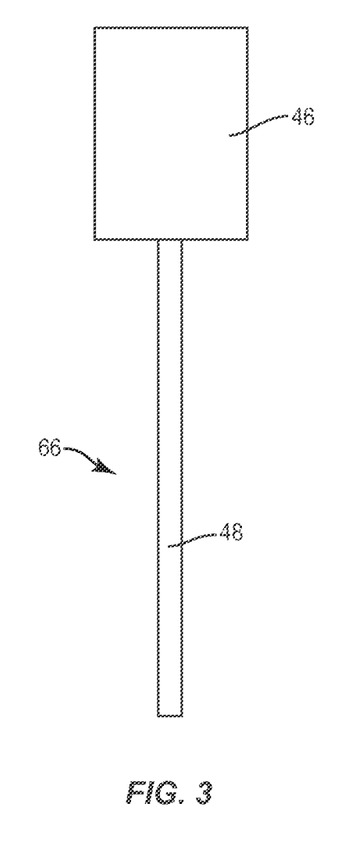
FIG. 3 is a side view of components of one embodiment of a spinal implant system in accordance with the principles of the present disclosure.

The following discussion includes a description of a surgical system including a surgical instrument/bone fastener assembly, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, to deliver and introduce one or more implants of a spinal construct at a surgical site within a body of a patient, for example, a section of a spine. In some embodiments, spinal implant system 10 may include and/or deliver and introduce implants such as spinal rods, bone fasteners, connectors, plates and interbody devices. Spinal implant system 10 includes one or more surgical instruments including an implant support, such as, for example, a percutaneous pedicle access instrument 12. In some embodiments, spinal implant system 10 may comprise various alternate surgical instruments, such as, for example, drivers, extenders, reducers, spreaders, distractors, blades, clamps, forceps, elevators and drills, which may be alternately sized and dimensioned, and arranged as a kit.

Pedicle access instrument 12, as shown in FIG. 1, is tubular and comprises a sleeve 14 that extends along a longitudinal axis X, and between a proximal end 16 and a distal end 18. Sleeve 14 has a cylindrical cross-section configuration. In some embodiments, the cross-section of sleeve 14 may have various configurations, for example, round, oval, rectangular, polygonal, irregular, tapered, offset, staggered, uniform and non-uniform. In some embodiments, one or all of the surfaces of sleeve 14 may have alternate surface configurations, such as, for example, rough, threaded for connection with surgical instruments, arcuate, undulating, porous, semi-porous, dimpled, polished and/or textured.

Sleeve 14 includes a wall surface that defines two spaced apart extensions, an extension 20 and an extension 22. Extensions 20, 22 are connected adjacent end 18. Extensions 20, 22 define a channel 24 extending between ends 16, 18. Channel 24 is configured for disposal of one or more components of spinal implant system 10, as described herein. Channel 24 has a cylindrical cross-section configuration. In some embodiments, the cross-section of channel 24 may have various configurations, for example, round, oval, rectangular, polygonal, irregular, tapered, offset, staggered, uniform and non-uniform.

The wall surface of sleeve 14 includes a portion 26 that is frangibly connected to a portion 28 adjacent break off elements 30 disposed with each of extensions 20, 22. Elements 30 each have reduced thickness and/or reduced diameter portion 32. In some embodiments, elements 30 are fabricated from a fracturing and/or frangible material such that manipulation of portion 26 relative to portion 28 can fracture and separate portion 26 from portion 28 at a predetermined force and/or torque limit, as described herein. In some embodiments, as force and/or torque is applied to extensions 20, 22 and resistance increases, for example, due to fixation of portion 28/bone fastener, as described herein, with tissue, the predetermined torque and force limit is approached.

In some embodiments, elements 30 can fracture and separate at a predetermined force or torque limit, which may be in a range of approximately 20 Newton centimeters (N-cm) to 50 N-cm. In some embodiments, elements 30 of extension 20 and/or extension 22 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of portions 26, 28. In some embodiments, manipulation of extensions 20, 22 to fracture and separate portion 26, 28 can include bending in a single plane. Other methods of separation between portions 26 and 28, such as releasable mechanical locking between the portions 26 and 28 may also be implemented. Such methods would still result in portion 28 remaining implanted and portion 26 being removed from the surgical site.

Figure 8:
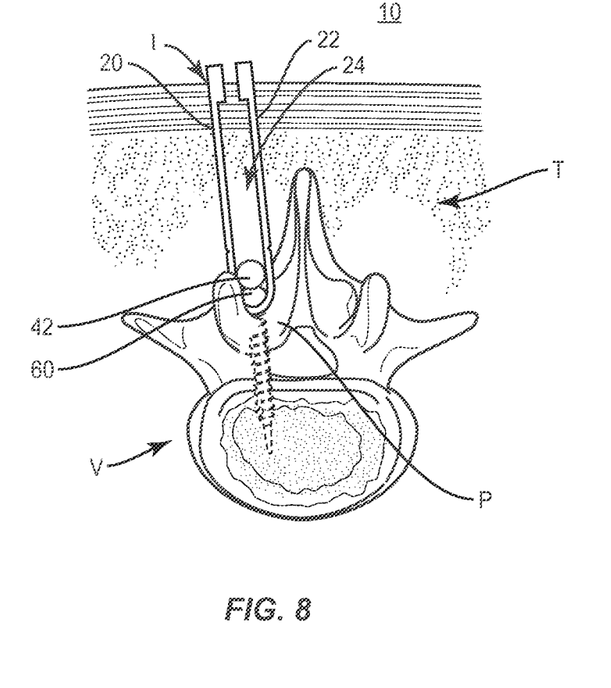
FIG. 8 is a side view of components of one embodiment of a spinal implant system in accordance with the principles of the present disclosure disposed with tissue.

Upon fracture and separation of portions 26, 28, as described herein, portion 28 comprises an implant receiver 34. Receiver 34 includes a pair of spaced apart arms 36, 38 that define an implant cavity 40 therebetween configured for disposal of a component of a spinal construct, such as, for example, a spinal rod 42 (FIG. 8). Arms 36, 38 each extend parallel to axis X. In some embodiments, arm 36 and/or arm 38 may be disposed at alternate orientations, relative to axis X, such as, for example, transverse, perpendicular and/or other angular orientations such as acute or obtuse, coaxial and/or may be offset or staggered. In some embodiments, arms 36, 38 each include an arcuate outer surface extending between a pair of side surfaces. In some embodiments, at least one of the outer surfaces and the side surfaces of arms 36, 38 have at least one recess or cavity therein configured to receive an insertion tool, compression instrument and/or instruments for inserting and tensioning a bone fastener comprising implant receiver 34. In some embodiments, arms 36, 38 are connected at proximal and distal ends thereof such that receiver 34 defines a partially closed or closed spinal rod slot.

Figure 9:
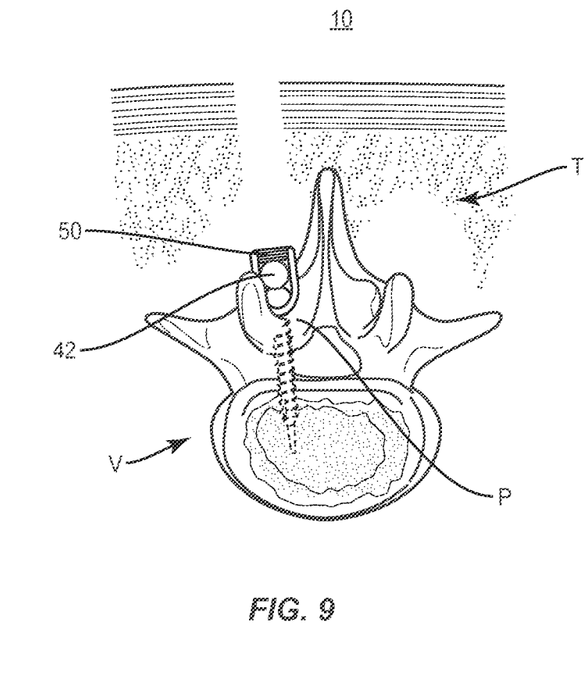
FIG. 9 is a side view of components of one embodiment of a spinal implant system in accordance with the principles of the present disclosure disposed with tissue.

Cavity 40 is substantially U-shaped. In some embodiments, all or only a portion of cavity 40 may have alternate cross section configurations, such as, for example, partially closed, closed, V-shaped, W-shaped, oval, oblong, triangular, square, polygonal, irregular, uniform, non-uniform, offset, staggered, and/or tapered. Receiver 34 includes an inner surface having a thread form located adjacent arm 36 and a thread form located adjacent arm 38. The thread forms are each configured for engagement with a coupling member, such as, for example, a setscrew 50 (FIG. 9), to retain a spinal construct, such as, for example, spinal rod 42 within cavity 40. In some embodiments, the inner surface of receiver 34 may be disposed with the coupling member in alternate fixation configurations, such as, for example, friction fit, pressure fit, locking protrusion/recess, locking keyway and/or adhesive. In some embodiments, all or only a portion of the inner surface of receiver 34 may have alternate surface configurations to enhance engagement with spinal rod 42 and/or setscrew 50 such as, for example, rough, arcuate, undulating, mesh, porous, semi-porous, dimpled and/or textured. In some embodiments, receiver 34 may include alternate configurations, such as, for example, partially closed, closed, open and/or side access.

Extensions 20, 22 are connected adjacent end 18. Extensions 20, 22 include end surfaces that define an opening 52 adjacent end 18. A member, such as, for example, a gasket 54 is fixed with opening 52 and configured to support a bone fastener 56, as shown in FIG. 2. In some embodiments, the member comprises a flexible membrane. Gasket 54 covers at least a portion of opening 52 and is attached with the end surfaces that define opening 52, as shown in FIG. 1. In some embodiments, gasket 54 allows end 18 to advance through tissue in an introduction position of pedicle access instrument 12. In some embodiments, gasket 54 resists and/or prevents tissue from moving into opening 52. Gasket 54 forms a seal with portion 28. In some embodiments, extensions 20, 22 are connected adjacent end 18 without a member.

In some embodiments, gasket 54 may be attached to end 18 with an adhesive. In some embodiments, gasket 54 may be permeable, porous, or semi-permeable or semi-porous. In some embodiments, gasket 54 may be fabricated from a material that is impermeable to prevent bone growth or leakage therethrough. In some embodiments, gasket 54 may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, gasket 54 may have a semi-rigid, rigid or elastic configuration, and/or have elastic properties, such as the elastic properties corresponding to the material examples described above. In some embodiments, gasket 54 may be fabricated from elastomeric materials such as, for example, mylar, rubber, polyurethane, vinyl, latex, polyethylenes, ionomer, and PET, as well as less flexible materials such as stainless steel, titanium, nickel-titanium alloy, and ceramic mesh or weaved materials and combinations thereof. In some embodiments, all or a portion of gasket 54 may be made permeable by fabricating a material, including the materials listed above, into a fabric, weave, mesh, composite, bonded fiber assembly. In some embodiments, gasket 54 can be a separate material or molded directly with extension 20 and/or extension 22.

Gasket 54 defines a flexible slot 58 that is movable between a closed and sealed position and an open position such that gasket 54 is moved to expose and/or establish communication with channel 24 and/or cavity 40. In some embodiments, bone fastener 56 is engageable with gasket 54 adjacent slot 58 to dispose slot 58 in the open position such that bone fastener 56 passes, punctures and/or translates through gasket 54. As bone fastener 56 is disposed with and/or passes through slot 58, the surface of slot 58 closely engages and/or creates a sliding seal with the surface of bone fastener 56. In some embodiments, this configuration stabilizes and/or orients bone fastener 56 for positioning with tissue, for example, access and tip exposure for penetrating a pedicle. In some embodiments, slot 58 resists and/or prevents bone fastener 56 from passing entirely through gasket 54 such that a head of bone fastener 56 is prevented from passing through gasket 54 and is retained within cavity 40. This configuration facilitates connection of bone fastener 56 with portion 28 to comprise a bone fastener 56/receiver 34 spinal construct attached with tissue.

In some embodiments, bone fastener 56 comprises a pedicle screw, as shown in FIG. 2. Bone fastener 56 includes a spherical head 60 and an elongated shaft 62 configured for penetrating tissue. Head 60 includes a socket 64 configured for disposal of a surgical instrument, such as, for example, an introducer/driver 66, as shown in FIG. 3. Introducer/driver 66 includes a handle 46 and a shaft 48 that engages socket 64 to rotate shaft 62, as described herein. In some embodiments, arms 36, 38 may be disposed at alternate orientations, relative to shaft 62, such as, for example, those alternatives described herein.

In some embodiments, shaft 62 has an access stylet tip 68. In some embodiments, shaft 62 has a trocar stylet tip. Shaft 62 has a cylindrical cross section configuration and includes an outer surface having an external thread form. In some embodiments, the external thread form may include a single thread turn or a plurality of discrete threads. In some embodiments, other engaging structures may be located on shaft 62, such as, for example, a nail configuration, barbs, expanding elements, raised elements and/or spikes to facilitate engagement of shaft 62 with tissue.

In some embodiments, all or only a portion of shaft 62 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 62 may include one or a plurality of openings. In some embodiments, all or only a portion of the outer surface of shaft 62 may have alternate surface configurations, such as, for example, smooth and/or surface configurations to enhance fixation with tissue, such as, for example, rough, arcuate, undulating, porous, semi-porous, dimpled, polished and/or textured. In some embodiments, all or only a portion of shaft 62 may be cannulated.

In some embodiments, bone fastener 56 is fixed with receiver 34 such that head 60 is retained with cavity 40 and shaft 62 extends therefrom in a selected movement that includes rotation and/or pivotal movement of shaft 62 relative to receiver 34 about one or a plurality of axes. In some embodiments, the selected movement includes rotation and/or pivotal movement of shaft 62 relative to receiver 34 through one or a plurality of planes. In some embodiments, shaft 62 is connected to receiver 34 to comprise a multi-axial fastener. In some embodiments, shaft 62 is connected to receiver 34 to comprise a uni-axial fastener. In some embodiments, shaft 62 is connected to receiver 34 to comprise a multi-axial screw, sagittal angulation screw, pedicle screw, mono-axial screw, uni-planar screw, facet screw, fixed screw, tissue penetrating screw, conventional screw, expanding screw, wedge, anchor, expanding rivet, staple, nail, and/or post. In some embodiments, spinal constructs comprising one or more of shaft 62 connected to receiver 34 may be engaged with tissue in various orientations, such as, for example, series, parallel, offset, staggered and/or alternate vertebral levels.

In some embodiments, spinal implant system 10 may include one or a plurality of spinal rods 42, which may be relatively disposed in a side by side, irregular, uniform, non-uniform, offset and/or staggered orientation or arrangement. In some embodiments, spinal rod 42 can have a uniform thickness/diameter. In some embodiments, spinal rod 42 may have various surface configurations, such as, for example, rough, threaded for connection with surgical instruments, arcuate, undulating, dimpled, polished and/or textured. In some embodiments, the thickness defined by spinal rod 42 may be uniformly increasing or decreasing, or have alternate diameter dimensions along its length. In some embodiments, spinal rod 42 may have various cross section configurations, such as, for example, oval, oblong, triangular, rectangular, square, polygonal, irregular, uniform, non-uniform, variable and/or tapered. In some embodiments, spinal rod 42 may have various lengths.

In some embodiments, spinal rod 42 may have a flexible configuration and be fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of spinal rod 42 includes movement in a lateral or side to side direction and prevents expanding and/or extension in an axial direction. In some embodiments, all or only a portion of spinal rod 42 may have a semi-rigid, rigid or elastic configuration, and/or have elastic properties, such as the elastic properties corresponding to the material examples described above. In some embodiments, spinal rod 42 may be compressible in an axial direction.

In some embodiments, pedicle access instrument 12, bone fastener 56 and introducer/driver 66 are connected, attached and/or assembled to comprise a pedicle access assembly of spinal implant system 10, as described herein, for percutaneous introduction and delivery to a surgical site. In some embodiments, an implant can include spinal constructs, such as, for example, receiver 34 connected with bone fastener 56, spinal rods 42, set screws 50, connectors and/or plates.

In some embodiments, spinal implant system 10 may comprise the use of microsurgical and image guided technologies, such as, for example, surgical navigation components employing emitters and sensors, which may be employed to track introduction and/or delivery of the components of spinal implant system 10 including pedicle access instrument 12 to a surgical site. See, for example, the surgical navigation components and their use as described in U.S. Pat. Nos. 6,021,343, 6,725,080, 6,796,988, the entire contents of each of these references being incorporated by reference herein.

In assembly, operation and use, spinal implant system 10, similar to the systems described herein, is employed with a surgical procedure for treatment of a spinal disorder, such as, for example, those affecting a section of a spine of a patient. In some embodiments, one or all of the components of spinal implant system 10 can be delivered or implanted as a pre-assembled device or can be assembled in situ. Spinal implant system 10 may be completely or partially revised, removed or replaced. For example, the pedicle access assembly described herein can be employed to treat degenerative disorders, deformity disorders, trauma, tumor and infection disorders, and advanced deformity disorders, and any combination thereof. In some embodiments, the pedicle access assembly can be employed to treat degenerative disorders such that the components of spinal implant system 10 engage spinal tissue along one or a plurality of vertebral levels.

To treat a selected section of vertebrae V, as shown in FIGS. 4-9, a medical practitioner obtains access to a surgical site including vertebrae V in any appropriate manner, such as through incision and retraction of tissue T. In some embodiments, spinal implant system 10 can be used in a percutaneous surgical implantation, whereby vertebrae V are accessed through a pedicle access assembly 100. In some embodiments, pedicle access assembly 100 can be employed with a mini-incision, or sleeve that provides a protected passageway to the area. Once access to the surgical site is obtained, the particular surgical procedure can be performed for treating the spine disorder.

A stab incision I is made in tissue T and a cutting instrument (not shown) creates a surgical pathway for delivery of components of spinal implant system 10 adjacent an area within the patient's body, such as, for example, vertebrae V.

In some embodiments, a pedicle access needle (not shown) is used to gain access to vertebrae V, and create a surgical pathway to the surgical site. The pedicle access needle is placed at the intersection of a facet and a transverse process adjacent to a pedicle P, and is advanced. In some embodiments, the needle may be advanced across the junction of pedicle P to allow easier placement of a guidewire (not shown). The guidewire is connected and/or fastened with tissue, such as, for example, pedicle P at a surgical site. The guidewire is fastened with pedicle P and disposed to extend along the surgical pathway from the surgical site adjacent pedicle P to incision I for a percutaneous surgical procedure. A preparation instrument (not shown) can be employed to prepare tissue surfaces of vertebrae V, as well as for aspiration and irrigation of a surgical region. In some embodiments, pilot holes or the like are made in pedicle P for receiving shaft 62 of pedicle screws 56.

In some embodiments, pedicle access instrument 12, as described herein, is provided for a selected surgical procedure. In some embodiments, a pedicle screw 56 is selected from a plurality of alternate pedicle screws 56, which are alternately sized and configured, for example, having multiple diameters and/or lengths available.

Figure 4:
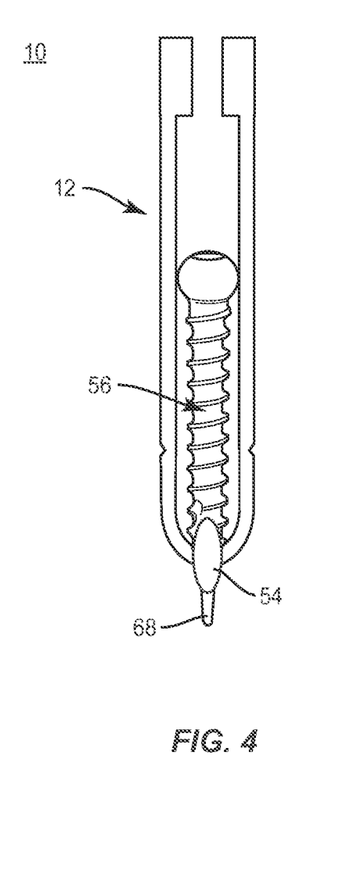
FIG. 4 is a side view of components of one embodiment of a spinal implant system in accordance with the principles of the present disclosure.

A selected pedicle screw 56, as shown in FIG. 4, is introduced to pedicle access instrument 12. Gasket 54 is disposed in a closed and sealed position, as described herein. Pedicle screw 56 engages gasket 54 adjacent slot 58 to dispose slot 58 in the open position such that pedicle screw 56 passes through gasket 54. The surface of slot 58 closely engages and/or creates a sliding seal with the surface of pedicle screw 56. Tip 68 extends beyond gasket 54 and is oriented for access and exposure for penetrating pedicle P. In some embodiments, pedicle screw 56 is passed through end 18 without a gasket. In some embodiments, pedicle screw 56 is cannulated for translation along the guidewire.

Figure 5:
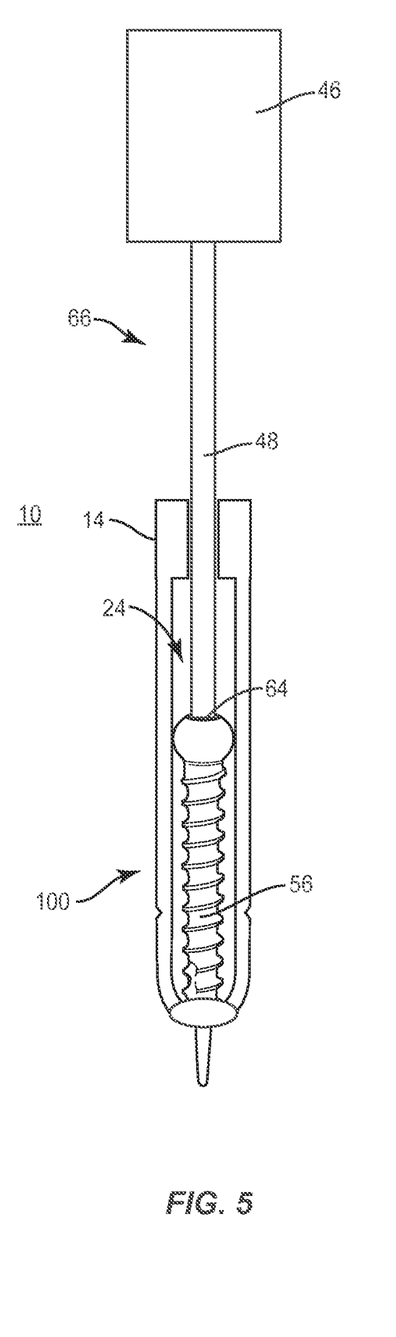
FIG. 5 is a side view of components of one embodiment of a spinal implant system in accordance with the principles of the present disclosure.

Handle 46 is manipulated and introducer/driver 66 is translated into channel 24 such that shaft 48 engages socket 64 for connection with sleeve 14 and pedicle screw 56, as shown in FIG. 5. Introducer/driver 66 is connected with pedicle access instrument 12 and pedicle screw 56 in a configuration to comprise pedicle access assembly 100.

Figure 6:
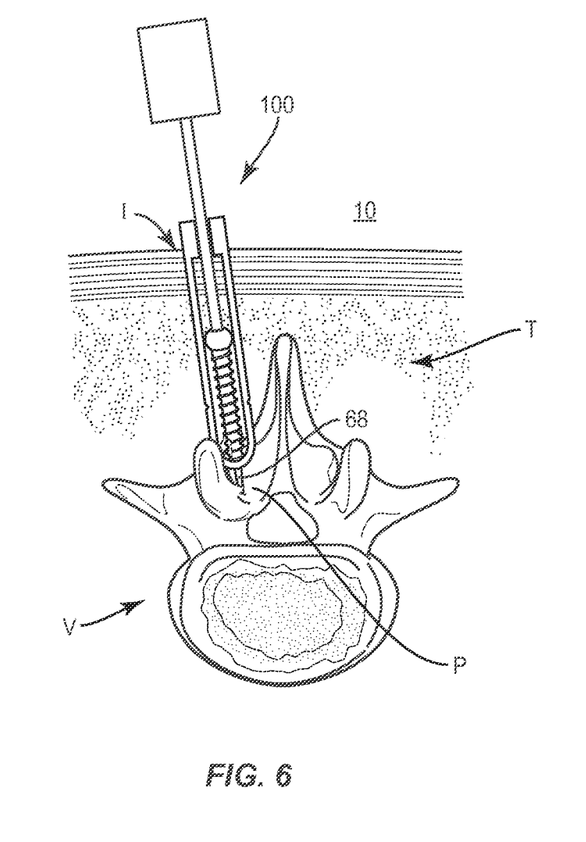
FIG. 6 is a side view of the components shown in FIG. 5 disposed with tissue.
Figure 7:
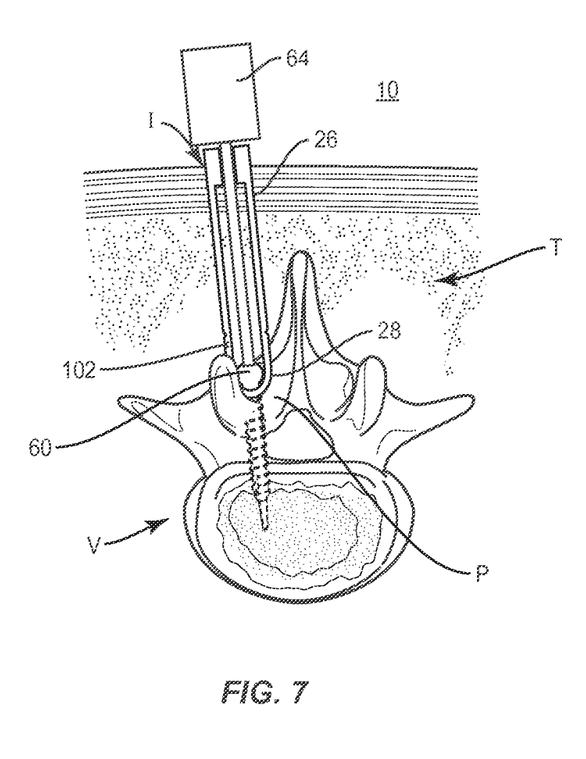
FIG. 7 is a side view of the components and tissue shown in FIG. 6.

Pedicle access assembly 100 is delivered through incision I along the surgical pathway to pedicle P such that tip 68 penetrates pedicle P, as shown in FIG. 6. Handle 64 is rotated to drive pedicle screw 56 into pedicle P with introducer/driver 66, as shown in FIG. 7. In some embodiments, portion 26 and/or portion 28 include one or more bone graft delivery windows 102 to minimally invasively deliver graft material adjacent the surgical site. Shaft 48 is disengaged from socket 64 and introducer/driver 66 is removed from the surgical site, as shown in FIG. 8.

Spinal rod 42 is delivered through incision I and along the pathway to the surgical site. Spinal rod 42 is inclined relative to extensions 20, 22 and disposed with channel 24 adjacent head 60. Set screw 50 is delivered through incision I and along the pathway to the surgical site. Set screw 50 is disposed with channel 24 adjacent spinal rod 42. In some embodiments, set screw 50 may be provisionally threaded with the inner surface of portion 28 to fix spinal rod 42 in position relative to vertebrae V.

Extensions 20, 22 are manipulated such that elements 30 are fractured at a predetermined force or torque limit, as described herein. Portion 26 fractures and separates from portion 28. Set screw 50 is threaded and tightened with receiver 34 to fix position of spinal rod 42 with pedicle P. Receiver 34 connected with pedicle screw 56, spinal rod 42 and set screw 50 comprise a spinal construct attached with pedicle P provided by pedicle access assembly 100.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be hydroxyapatite coating. In some embodiments, the agent may include one or a plurality of therapeutic agents and/or pharmacological agents for release, including sustained release, to treat, for example, pain, inflammation and degeneration.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method of treating a spine, the method comprising the steps of:
    providing an implant support including a first portion connected to a second portion that defines an implant cavity and supports a bone fastener;
    connecting a surgical introducer instrument with the implant support and engaging the surgical introducer instrument with the bone fastener such that a distal end of the bone fastener is generally adjacent the second portion;
    percutaneously introducing the surgical introducer instrument, implant support and bone fastener to a surgical site including tissue;
    extending the bone fastener through the second portion and into bone generally adjacent the second portion;
    disposing a spinal rod with the implant cavity;
    removing the first portion from the second portion; and
    mating threads of a setscrew with threads of the second portion such that the set screw engages the spinal rod to fix the spinal rod relative to the bone,
    wherein the implant support further includes a relatively flexible member that supports the bone fastener, and
    wherein the member comprises a gasket and further including the step of engaging the second portion with the gasket to seal the implant cavity.

2. A method as recited in claim 1, wherein the step of providing includes extending a tip of the bone fastener from the second portion.

3. A method as recited in claim 1, wherein the step of providing includes selecting a bone fastener from a plurality of alternate bone fasteners.

4. A method as recited in claim 1, wherein the step of attaching includes attaching the bone fastener with a pedicle.

5. A method as recited in claim 1, further comprising the step of delivering bone graft to the surgical site via the second portion.

6. A method as recited in claim 1, further comprising the step of removing the surgical introducer instrument from the assembly.

7. A method as recited in claim 1, wherein:
    the implant support comprises a frangible connection having a reduced thickness that connects the first portion and the second portion; and
    the step of removing includes fracturing the frangible connection at a selected torque limit.

8. A method as recited in claim 1, wherein the first portion is removed from the second portion after the spinal rod is disposed with the implant cavity.

9. A method as recited in claim 1, wherein the step of disposing includes positioning the spinal rod such that the spinal rod engages a head of the bone fastener and an inner surface of the second portion that defines the implant cavity.

10. A method as recited in claim 1, wherein the step of extending includes engaging a spherical head of the bone fastener with an inner surface of the second portion that defines the implant cavity.

11. A method as recited in claim 1, wherein the step of extending includes penetrating the bone with an access stylet tip of the bone fastener.

12. A method of treating a spine, the method comprising the steps of:
    providing an implant support including a first portion connected to a second portion including an inner surface that defines an implant cavity;
    connecting a surgical introducer instrument with the implant support and engaging the surgical introducer instrument with a bone fastener such that a distal end of the bone fastener is generally adjacent the second portion;
    percutaneously introducing the surgical introducer instrument, implant support and bone fastener to a surgical site including tissue;
    extending the bone fastener through the second portion such that a shaft of the bone fastener penetrates bone and a head of the bone fastener engages the inner surface, the head being fixed relative to the shaft; and
    removing the first portion from the second portion after the step of extending,
    wherein the implant support further includes a relatively flexible member that supports the bone fastener, and wherein the member comprises a gasket and further including the step of engaging the second portion with the gasket to seal the implant cavity.

13. A method as recited in claim 12, wherein:
the implant support comprises a frangible connection having a reduced thickness that connects the first portion and the second portion; and
the step of removing includes fracturing the frangible connection.

14. A method as recited in claim 12, further comprising mating threads of a setscrew with threads of the second portion.

15. A method as recited in claim 12, wherein the step of extending includes penetrating the bone with an access stylet tip of the bone fastener.

16. A method of treating a spine, the method comprising the steps of:
providing an implant support including a first portion connected to a second portion that defines an implant cavity and supports a bone fastener;
connecting a surgical introducer instrument with the implant support and engaging the surgical introducer instrument with the bone fastener such that a distal end of the bone fastener is generally adjacent the second portion;
percutaneously introducing the surgical introducer instrument, implant support and bone fastener assembly to a surgical site including tissue;
extending the bone fastener through the second portion and into bone generally adjacent the second portion; and
removing the first portion from the second portion,
wherein the implant support further includes a relatively flexible member that supports the bone fastener, and
wherein the member comprises a gasket and further including the step of engaging the second portion with the gasket to seal the implant cavity.

* * * * *

UNITED STATES PATENT AND TRADEMARK OFFICE
CERTIFICATE OF CORRECTION

| | | |
|---|---|---|
| PATENT NO. | : 9,848,928 B2 | |
| APPLICATION NO. | : 14/627202 | |
| DATED | : December 26, 2017 | |
| INVENTOR(S) | : Foley et al. | |

It is certified that error appears in the above-identified patent and that said Letters Patent is hereby corrected as shown below:

In the Specification

In Column 11, Line 3, delete "Handle 64" and insert -- Handle 46 --, therefor.

Signed and Sealed this
Twelfth Day of June, 2018

Andrei Iancu
*Director of the United States Patent and Trademark Office*